United States Patent [19]
Woskov et al.

[11] Patent Number: 5,479,254
[45] Date of Patent: Dec. 26, 1995

[54] CONTINUOUS, REAL TIME MICROWAVE PLASMA ELEMENT SENSOR

[76] Inventors: Paul P. Woskov, 4 Ledgewood Dr., Bedford, Mass. 01730; Donna L. Smatlak, 10 Village Hill Rd., Belmont, Mass. 02178; Daniel R. Cohn, 26 Walnut Hill Rd., Chestnut Hill, Mass. 02167; J. Kenneth Wittle, 1740 Conestoga Rd., Chester Springs, Pa. 19425; Charles H. Titus, 323 Echo Valley La., Newtown Square, Pa. 19072; Jeffrey E. Surma, 806 Brian La., Kennewick, Wash. 99337

[21] Appl. No.: 141,857

[22] Filed: Oct. 22, 1993

[51] Int. Cl.$^6$ .............................. G01J 3/30; H01P 1/00; G01N 21/69
[52] U.S. Cl. ......................... 356/316; 333/99 PL
[58] Field of Search ......................... 356/316; 333/99 PL

[56] References Cited

U.S. PATENT DOCUMENTS

| | | | |
|---|---|---|---|
| 4,933,650 | 6/1990 | Okamoto | 333/99 PL |
| 4,965,540 | 10/1990 | Sullivan | 333/99 PL X |
| 5,211,142 | 5/1993 | Matthews et al. | 123/143 B |
| 5,262,610 | 11/1993 | Huang et al. | 219/121.43 |
| 5,270,616 | 12/1993 | Itatani | 315/111.21 |

OTHER PUBLICATIONS

Goode et al, "A Review of Instrumentation Used to Generate Microwave–Induced Plasmas," Applied Spectroscopy, vol. 38, No. 6, Nov.–Dec./1984.
Beenakker et al, "An Assessment of a Microwave–Induced Plasma . . . Solutions," Spectrochimica Acta, vol. 33, 1978.
M. W. Blades et al., "Application of Weakly Ionized Plasmas for Materials Sampling and Analysis", IEEE Trans. on Plasma Sci., vol. 19, pp. 1090–1113, 1991.
F. C. Fehsenfeld, et al., "Microwave Discharge Cavities Operating at 2450 MHz", Rev. of Sci. Instrm., vol. 36, pp. 294–298, 1965.
H. Matusiewicz, "A Novel Microwave Plasma Cavity Assembly for Atomic Emission Spectrometry", Spectrachimica Acta. vol. 47B, pp. 1221–1227, 1992.
Y. Okamoto, "Annular–Shaped Microwave–Induced Nitrogen Plasma at Atmospheric Pressure for Emission Spectrometry of Solutions", Analytical Sciences, vol. 7, pp. 283–288, 1991.
D. K. Smith and D. L. Smatlak, "Microwave Atmospheric Pressure Plasma Torch, Characteristics and Application", 27th Microwave Symposium, Washington, D.C., Aug. 2–5, 1992.
K. A. Forbes et al., "Comparison of Microwave–Induced Plasma Sources", J. of Analytical Atomic Spectrometry, vol. 6, pp. 57–71, 1991.
J. P. Matousek et al., "Microwave–Induced Plasmas: Implementation and Application", Prog. Analyt. Atom. Spectrosc., vol. 7, pp. 275–314, 1984.
S. R. Goode and K. W. Baughman, "A Review of Instrumentation Used to Generate Microwave–Induced Plasmas", Applied Spectrosc., vol. 38, pp. 755–763, 1984.
A. T. Zander and G. M. Hieftje, "Microwave–Supported (List continued on next page.)

Primary Examiner—Vincent P. McGraw
Assistant Examiner—K. P. Hantis
Attorney, Agent, or Firm—Choate, Hall & Stewart

[57] ABSTRACT

Microwave-induced plasma for continuous, real time trace element monitoring under harsh and variable conditions. The sensor includes a source of high power microwave energy and a shorted waveguide made of a microwave conductive, refractory material communicating with the source of the microwave energy to generate a plasma. The high power waveguide is constructed to be robust in a hot, hostile environment. It includes an aperture for the passage of gases to be analyzed and a spectrometer is connected to receive light from the plasma. Provision is made for real time in situ calibration. The spectrometer disperses the light, which is then analyzed by a computer. The sensor is capable of making continuous, real time quantitative measurements of desired elements, such as the heavy metals lead and mercury.

24 Claims, 2 Drawing Sheets

OTHER PUBLICATIONS

Discharges", Applied Spectrosc., vol. 35, pp. 357–371, 1981.

T. Ishizuka and Y. Uwamino, "Atomic Emission Spectrometry of Solid Samples with Laser Vaporization–Microwave Induced Plasma System", Anal. Chem., vol. 52, pp. 125–129, 1980.

Bacharach Instrument Co. (Pittsburgh, Pa.), produce description for "J–W Mercury Vapor Sniffer", no date.

Pacific Northwest Laboratory, Technology Brief for "Spectrochemical Emission Sensor".

Barnes et al, "Design Concepts for Stripline Microwave Spectro Chemical Sources," Anal. Chem. vol. 62, No. 23, Dec. 1, 1990, pp. 2650–2654.

Demirgian, "Continous Emission Monitor For Incinerators," U.S. Depart. of Energy Info. Exchange Meeting on the Characterization, Monitoring and Sensor Technologies, Dallas, Texas Jun. 3–4, 1992.

CONTINUOUS, REAL TIME MICROWAVE PLASMA ELEMENT SENSOR

This invention was made with government support under Contract Number DE-AC06-76RLO 1830 awarded by the Department of Energy. The government has certain rights in the invention.

BACKGROUND OF THE INVENTION

This invention relates to method and apparatus for analyzing elemental composition of furnace off-gasses, and more particularly to method and apparatus for continuous, real time monitoring of the elemental content of furnace off-gasses using a microwave-induced plasma and atomic emission spectroscopy which could be implemented in situ.

In the global effort to protect the environment, there exists the need to monitor exhaust gases from all types of furnaces to detect the emission of hazardous chemicals. It is desirable that such a monitoring device be capable of continuous, real time application under harsh and variable conditions. In particular, location in situ or close proximity in the furnace off-gas stream would facilitate accurate spatially resolved measurements. It is also desired that such a monitoring device be able readily to detect the presence of hazardous elements, such as trace metals including lead, mercury, arsenic, beryllium, chromium, antimony, barium, cadmium, thallium, nickel, selenium, and silver as soon as they appear in the exhaust gas and at levels below Environmental Protection Agency mandated threshold levels. Such a device must also be useable in or in close proximity to the hot, dirty environment of a furnace and be capable of detecting the presence of many different elements simultaneously.

Instrumentation for the sensitive analysis of materials developed to date suffer from limitations including their not being true continuous, real time devices, not applicable to in situ measurements, not capable of detecting trace metals, or being limited to monitoring only one element at a time. The use of plasma sources for elemental excitation or detection is currently the primary means for detection of trace elements in solids, liquids and gasses. M.W. Blades, P. Banks, C. Gill, D. Huang, C. Le Blanc, and D. Liang, Application of Weakly Ionized Plasmas for Materials Sampling and Analysis, *IEEE Trans. on Plasma Sci.*, Vol. 19, pp. 1090–1113, 1991 have reviewed such technology, which included conductively coupled plasmas, microwave-induced plasmas, and other techniques. None of the techniques so described are applicable to continuous, real time in situ measurements. Fast Fourier transform spectroscopy, as described by J. Demirgian, Continuous Monitor for Incinerators, U.S. Department of Energy Information Exchange Meeting on the Characterization, Monitoring, and Sensor Technologies, Dallas, TX, June 3–4, 1992 can be used for continuous, near real time monitoring of molecular gases, but is not capable of the detection of metals, especially if the metals are in particulate form. Commercial in situ detectors, such as the Bacharach Instrument Company mercury sniffer model MV-2J-W and the Pacific Northwest Laboratory Halo-sniff spectrochemical emission sensor are limited to detecting only one element at a time. Further, these devices cannot be used for continuous, real time measurements of metals in a wide range of particulate as well as vapor form in a furnace environment. They must pull in a gas sample through a pipe and/or small orifice, which if used in a hot exhaust environment could give false results due to condensation or blockage due to larger particulates.

F.C. Fehsenfeld, K.M. Evenson, and H.P. Broida, Microwave Discharge Cavities Operating at 2450 MHz, Rev. of Sci. Instrm., Vol. 36, pp. 294–298, (1965) described a number of microwave-induced plasma (MIP) resonator cavity structures. One such structure had a built in taper to reduce its height to increase the electric field strength for plasma breakdown. This device was a resonator, not a shorted wave guide. It also included a number of features that limited maximum microwave power, such as a cable connection to the source of such power. None of the devices described by Fehsenfeld can be used in a furnace environment.

R.M. Barnes and E.E. Reszke, Design Concepts for Strip-Line Microwave Spectrochemical Sources, Anal. Chem., Vol. 62, pp. 2650–2654, (1990) described a shorted strip-line microwave MIP arrangement with a dielectric tube through the device one-quarter wavelength from the shorted end. Again, the features of this device, such as the presence of the strip-line and the cable connection to the source, would limit the maximum power operation of this device. Furthermore, this device could not be used in the hot, dirty furnace exhaust environment.

H. Matusiewicz, A Novel Microwave Plasma Cavity Assembly for Atomic Emission Spectrometry, Spectrachimica Acta, Vol. 47B, pp. 1221–1227, (1992); Y. Okamoto, Annular-Shaped Microwave-Induced Nitrogen Plasma at Atmospheric Pressure for Emission Spectrometry of Solutions, Analytical Science, Vol. 7, pp. 283–288, (1991); and D.K. Smith and D.L. Smatlak, Microwave Atmospheric Pressure Plasma Torch, Characteristics and Application, 27th Microwave Symposium, Washington, D.C., Aug. 2–5, 1992 described higher power MIP devices connected to the microwave source directly by wave guide. These devices utilize dielectric tubes and lack the provision for remote calibration, ignition or heating, which make them unsuitable for use in a furnace environment.

Other microwave-induced plasma-atomic emission spectroscopy devices are described by K.A. Forbes, E.E. Reszle, P.C. Uden, and R.M. Barnes, Comparison of Microwave-Induced Plasma Sources, J. of Analytical Atomic Spectrometry, Vol. 6, pp. 57–71, 1991; J.P. Matousek, B.J. Orr, and M. Selby, Microwave-Induced Plasmas: Implementation and Application, Prog. Analyt. Atom. Spectrosc., Vol. 7, pp. 275–314, 1984; S.R. Goode and K.W. Baughman, A Review of Instrumentation Used to Generate Microwave-Induced Plasmas, Applied Spectrosc., Vol. 38, pp. 755–763, 1984; and A.T. Zander and G.M. Hieftje, Microwave-Supported Discharges, Applied Spectrosc., Vol. 35, pp. 357–371, 1981.

Real time, remote calibration is also an important feature for any continuous, real time MIP device which must operate over a variable range of gas flow composition. A furnace off-gas stream will consist of the main working gas, such as air or nitrogen, along with a variable and not-well characterized waste off-gas. Atomic emission line intensities depend, in part, on the plasma gas mixture (matrix effect). This makes in situ calibration necessary for quantitative measurements. The use of laser ablation to introduce samples for calibration purposes into an MIP device has been described by T. Ishizuka and Y. Uwamino, Atomic Emission Spectrometry of Solid Samples with Laser Vaporization-Microwave Induced Plasma System, Anal. Chem., Vol. 52, pp. 125–129, (1980). However, this device would not work for remote calibration because an absolute calibration is required, not the relative one for which the Ishizuka et al. device was designed. In the Ishizuka et al. device, tubing between the laser ablation plate and the plasma causes much of the laser sputtered material to condense out making an absolute calibration unreliable.

SUMMARY OF THE INVENTION

The microwave-induced plasma element sensor according to the invention includes a source of microwave energy and a shorted waveguide made of a microwave conductive material, which may be a poor dc electrical conductor, communicating with the source of the microwave energy to generate a plasma. The waveguide includes an aperture for the passage of the gasses to be analyzed and a spectrometer is connected to receive light from the plasma. The spectrometer analyzes the received light spectrum to identify elements. In a preferred embodiment, the portion of the waveguide exposed to the furnace gasses is made of refractory material and may be an open mesh. Provision is made to heat this portion of the waveguide to prevent furnace gas condensation. This embodiment includes a retractable ignitor for igniting the plasma or reigniting it, if necessary during operation. A calibration apparatus is provided to perform an absolute calibration so that quantitative measurements can be made. It is also preferred that structure be included to create turbulence in the plasma which helps to localize the plasma in the waveguide where plasma operation is optimized. The waveguide may also include impedance matching. It is also preferred that the waveguide be tapered to intensify further the electric field to aid plasma breakdown. It is preferred that the refractory material be graphite or molybdenum and the refractory may be lined or coated with non-oxidizing materials for operation in a hot oxidizing environment. The spectrometer may be a Czerny-Turner grating spectrometer. Fiber optics are preferred for transmission of the plasma light to the spectrometer. For in situ operation the fiber optics would be unclad quartz or equivalent optical/untransmitting, high temperature material for robust in a hot environment.

The calibration system includes an alloy plate including elements of interest and a laser having a power selected to eject known masses of matrice for calibration purposes. In the preferred embodiment the laser beam is transmitted by fiber optics to the calibration plate. Alternative remote calibration configurations include the use of electric sparks, aerosols or gaseous calibration sources.

The sensor of the present invention is well-suited to real time in situ operation in that the refractory materials and robust fiber optics can operate in the hostile environment of the furnace exhaust gases. The present configuration does not require a dielectric tube through the device to confine the gas flow in the plasma, as required in prior art MIP devices. Such tubes are typically made of quartz, boron nitrite or other high temperature nonmicrowave absorbing materials and are detrimental in an in situ device since they are subject to clouding (blocking the plasma light) in a dirty furnace off-gas environment.

DESCRIPTION OF THE PREFERRED EMBODIMENT

Figure 1:
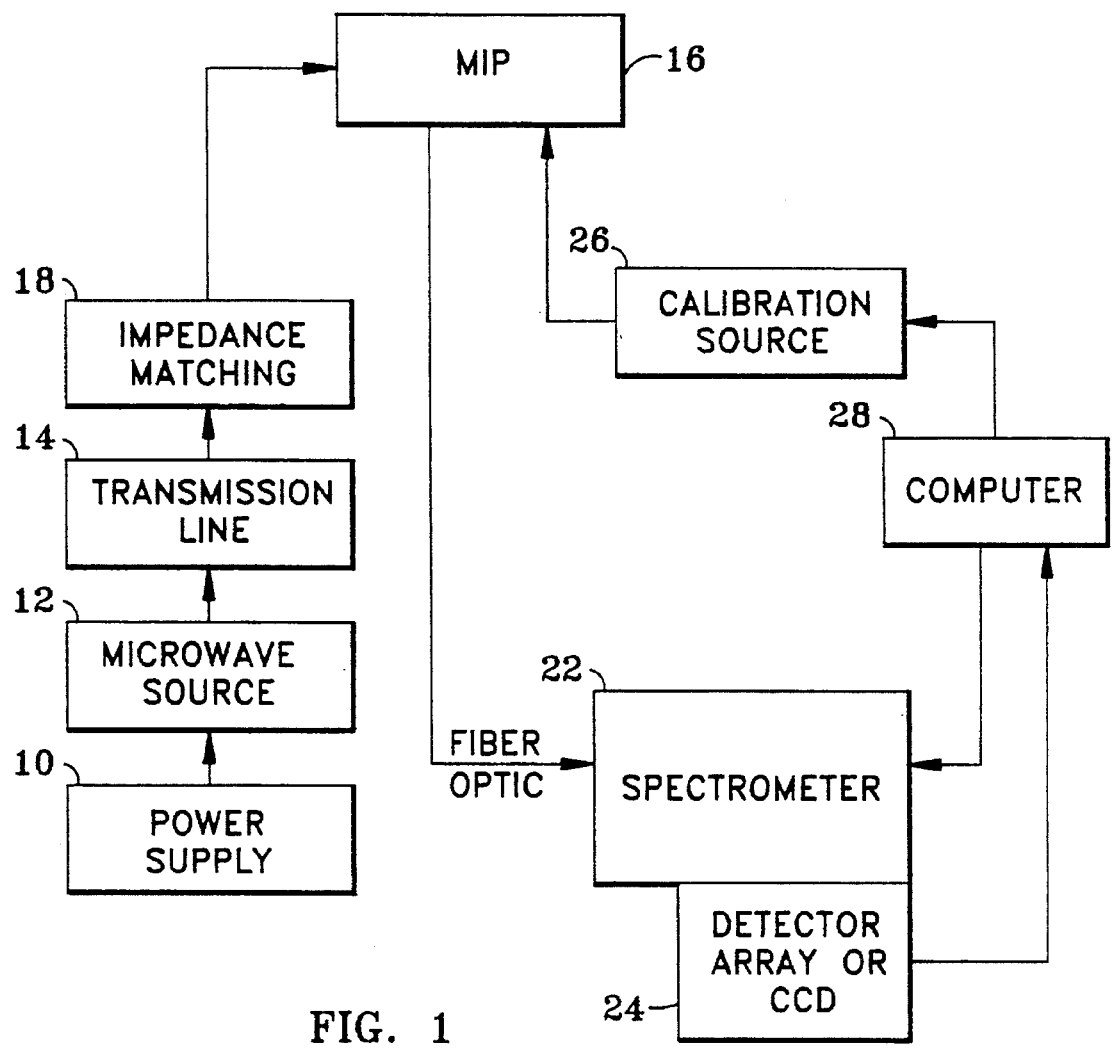
FIG. 1 is a block diagram of the microwave-induced plasma-atomic emission spectroscopy element analysis system of the invention.

FIG. 1 illustrates the major components of a microwave induced plasma - atomic emission spectroscopy element analysis system of the present invention. A power supply 10 powers a microwave source 12 with output powers greater than 300 Watts. An example of such a source is a magnetron. The high power level of the present invention is an advantage for robust operation in an in situ environment with variable gas mixes. The output of the microwave source 12 is transmitted by a transmission line 14 such as a waveguide to the plasma 16 through an impedance matching device 18. An impedance matching device may be a triple stub or an E-H tuner. An impedance matching device provides maximum transfer of energy from the source to the load by minimizing reflection and distortion. The source output interacts with the plasma support gas, such as Air or Nitrogen, which flows upstream through the transmission line creating plasmas which are ionized gas molecules and electrons. Plasmas, in turn, interact with particulates, compounds and atoms in the off-gas stream and produce excited atoms. As the excited atoms decay, plasma light is emitted. The emitted plasma light which spans from the ultraviolet (180 nm) through near infrared (2000 nm) is transmitted by a fiber optic cable 20 to a spectrometer 22 such as a Czerny Turner grating configuration. A detector array 24 such as a silicon linear diode array or a charge coupled device array is used to instantaneously detect the dispersed plasma spectrum over a part of the plasma light spectrum. The part of the plasma spectrum that can be instantaneously detected depends on the dispersion of the spectrometer and the size of the detector array. For example, a 0.62 m Czerny Turner grating spectrometer with a 2400 groove/mm grating and a 512 diode detector array will instantaneously detect approximately a 6.5 nm spectral band with 0.01 nm resolution. The grating can be rotated to access other portions of the spectrum. A calibration source 26 which can inject a known quantity of elements to be monitored is used to calibrate the emission levels for quantitative measurements. A computer 28 acquires the detector array data, controls the spectrometer tuning, and operates the calibration source.

Figure 2:
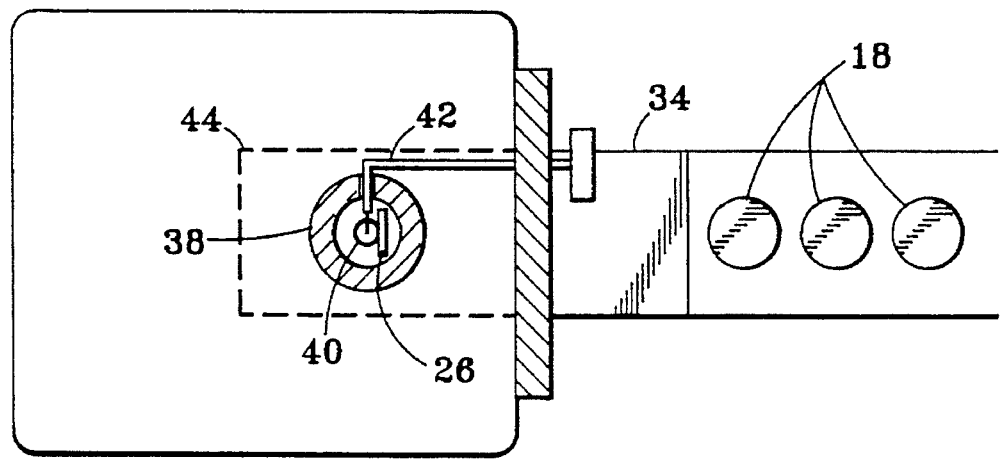
FIG. 2 is a side view of the apparatus of the invention.
Figure 3:
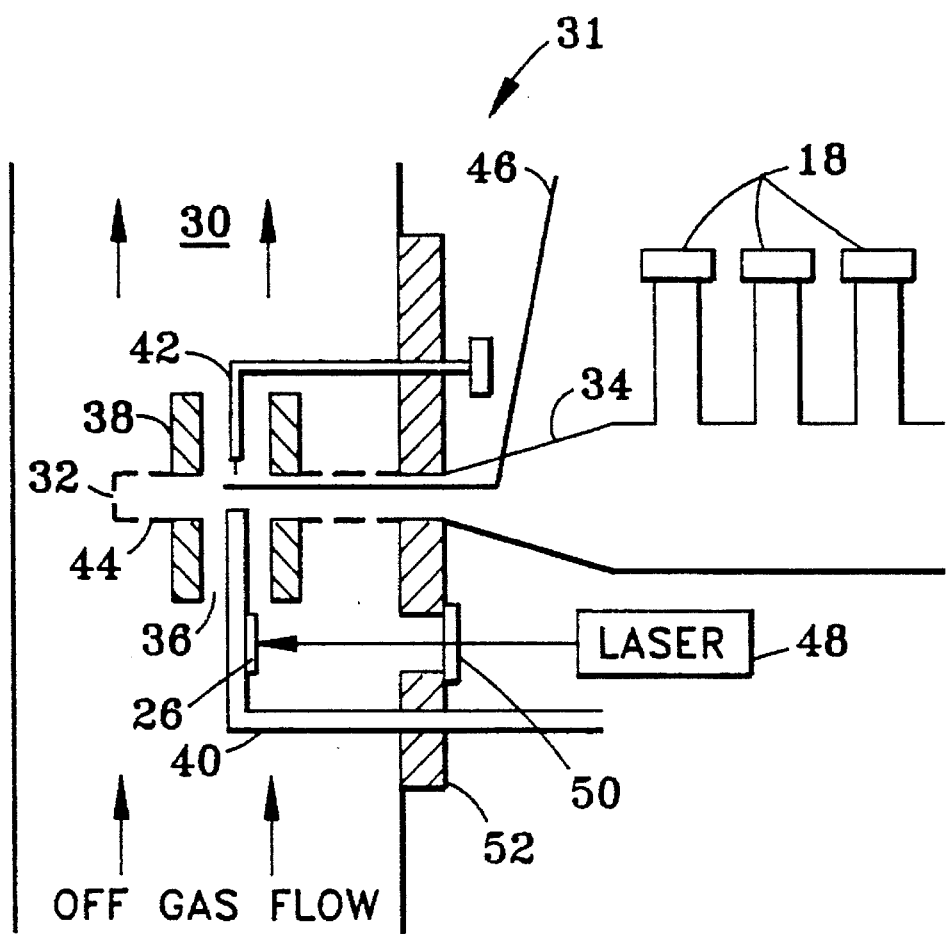
FIG. 3 is a top view of the apparatus of the invention.
Figure 2:
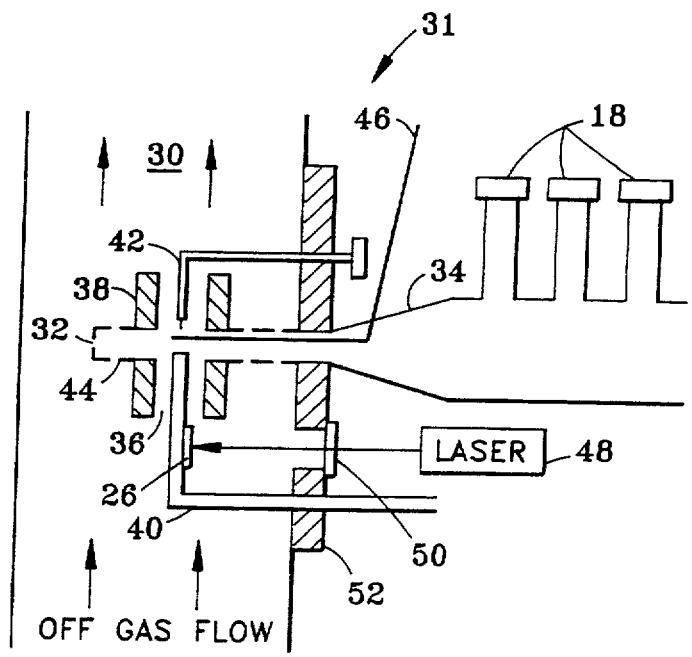
Figure 3:
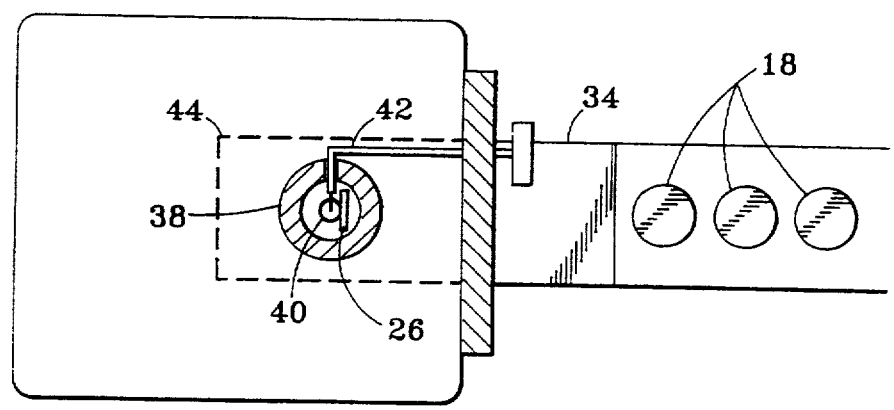

FIGS. 2 and 3 illustrate the details of the microwave induced plasma element sensor 31 of the invention. The sensor is placed in an off-gas flow stream 30 of a furnace (not shown). As discussed above, output from the microwave source 12 transmits through the waveguide 14 via an impedance matching device 18. The waveguide 14 is tapered 34 and shorted at one end 32. The plasma is created inside the shorted waveguide wherein the standing wave electric field is peaked at a distance $\frac{1}{4}\lambda_g$ from the shorted end 32 of the waveguide 14, where $\lambda_g$ is the guide wavelength for the microwave source power. To further intensify the electric field for plasma breakdown, the height of the waveguide is reduced relative to the transmitting waveguide through the waveguide taper 34. However, it is also possible to operate this plasma without a reduced waveguide. The direction of the electric field is parallel to the waveguide short wall dimension, which is also the direction of the gas flow 30 through the guide. A passageway 36 through the waveguide walls at the plasma location allow for a clear flow of the gases through the plasma region and removes solid material contact with the plasma. The aperture of the passageway 36 is less than $\frac{1}{4}\lambda_o$, where $\lambda_o$ is the free space wavelength of the microwave source power. Tubular structures 38 made of a microwave conducting material extend outward beyond the passageway 36 in both directions. These tubes 38 localize the gas flow through the plasma region and act as cutoff waveguides to prevent microwave leakage. The tube is constructed from refractory conductor material such as graphite, molybdenum or other suitable material. The MIP sensor structure 31 can be placed in a hot hostile furnace environment as a result of using a refractory material. To be used in a hot, oxidizing environment, the material could be lined or coated with non-oxidizing materials. In addition, the use of refractory materials along with the placement in a flowing gas stream eliminates the need for a quartz, boron nitrite, or other high temperature, non-microwave absorbing tube inserted completely through the microwave structure which is a feature of all other prior art MIP devices. The dielectric tube in prior art MIP devices is detrimental to an in situ device because it is subject to clouding in a dirty furnace off-gas environment.

An obstruction such as an alumina tube 40 inserted into the waveguide through the passageway 36 on the input gas flow side of the guide 14 creates turbulence in the gas flow which additionally localizes the plasma in the center of the passageway 36. A retractable igniter 42 is inserted through the upper part of the passageway 36 to initiate plasma breakdown when the microwave power is first turned on or if the plasma goes out during operation. When the plasma is on, this igniter is retracted or rotated out of the way. In this embodiment, the retractable igniter is an insulating rod such as alumina with a short length of wire (not shown) at its tip. The wire concentrates the electric field. Other remote ignition techniques are also possible such as an electric or laser spark.

It is preferred that the waveguide 14 which is within the gas stream 30 be made from an open and/or aerodynamically streamlined mesh 44. The open mesh 44 configuration and/or aerodynamic streamlining reduces blockage of the off gas stream flow. In addition, a mesh configuration allows more flexibility for viewing plasma emission light. The open mesh 44 is also made of a refractory material such as graphite or molybdenum. A fiber optic 46 attached to the outside of the waveguide 14 in the vicinity of the plasma transmits the emission light to the spectrometer 22 (FIG. 1). However, a closed waveguide with an appropriate hole or holes for the fiber optic can also be used.

The present invention also includes the provision for remote calibration. This is an important feature for a continuous, real time MIP device which must operate over a variable range of gas flow composition. A furnace off gas stream consists of the main working gas such as air or nitrogen along with a waste off gas that is variable and not well characterized. As atomic emission line intensities depend, in part, on the plasma gas mixture, in situ calibration is necessary for precise quantitative measurements. In a preferred embodiment, calibration is provided by a laser 48 which ablates a solid plate 26 with a known mix of elements to be analyzed. This plate may be an alloy of heavy metals. The plate is located on the gas input side of the waveguide 14 as close as possible to the plasma. A laser beam is focused onto the plate through a window 50 on the MIP element sensor mounting flange 52 to eject an amount of material which is determined in advance. The ablation laser 48 can be pulsed as often as needed to maintain the MIP sensor calibration. Although remote calibration is described in terms of free space propagation laser ablation, an alternative remote calibration configuration such as the use of fiber optics to bring in the laser beam, the use of electric sparks, and gaseous calibration sources directed into the plasma through the alumina tube may also be used.

What is claimed is:

1. Microwave-induced plasma element comprising:
   a source of microwave energy;
   a shorted waveguide made of a microwave conductive material using refractory material communicating with the source of the microwave energy to generate plasma, the waveguide including an aperture for the passage of gasses to be analyzed; and
   a spectrometer connected to receive light from the plasma.

2. The microwave-induced plasm element of claim 1 wherein a portion of the waveguide is an open mesh.

3. The microwave-induced plasm element of claim 1 wherein a portion of the waveguide is aerodynamically streamlined.

4. The microwave-induced plasma element of claim 1 further including a retractable ignitor for igniting and reigniting the plasma.

5. The microwave-induced plasma element of claim 1 further including calibration apparatus.

6. The microwave-induced plasma element of claim 1 further including structure near the plasma for inducing turbulence in the gasses to be analyzed.

7. The microwave-induced plasma element of claim 1 wherein the waveguide includes impedance matching structure.

8. The microwave-induced plasma element of claim i wherein the waveguide is tapered to intensify electric fields.

9. The microwave-induced plasma element of claim 1 wherein the source of microwave energy has an output greater than 300 watts.

10. The microwave-induced plasma element of claim 8 wherein the microwave source is a magnetron.

11. The microwave-induced plasma element of claim 1 wherein the shorted waveguide includes a shorted end such that standing wave electric field is peaked at a distance of $0.25\ \lambda_g$ from the shorted end of the shorted waveguide, wherein $\lambda_g$ is the guide wavelength of the microwave source power.

12. The microwave-induced plasma element of claim 1 wherein the aperture for the passage of gasses has a diameter of less than $0.25\ \lambda_o$, where $\lambda_o$ is the free space wavelength microwave source power.

13. The microwave-induced plasma element of claim 1 wherein the aperture for the passage of gases in the waveguide includes tubular structures extending outward therefrom, the tubular structures being constructed from refractory material.

14. The microwave-induced plasma element of claim 6 further including an impedance matching apparatus having a triple stub tuner.

15. The microwave-induced plasma element of claim 1 wherein a portion of the shorted waveguide exposed to the plasma is constructed from a refractory conductor material.

16. The microwave-induced plasma element of claim 12 wherein the waveguide is made of graphite.

17. The microwave-induced plasma element of claim 13 wherein the refractory conductor material is molybdenum.

18. The microwave-induced plasma element of claim 1 wherein the refractory material is coated with non-oxidizing materials for operation in a hot, oxidizing environment.

19. The microwave-induced plasma element of claim 1 wherein the spectrometer has a Czerny-Turner grating configuration.

20. The microwave-induced plasma element of claim 1 further including unclad fiber optics for transmitting plasma light to the spectrometer.

21. The microwave-induced plasma element of claim 1 further including a calibration plate including at least one element; and
   a laser for illuminating the plate to eject material for analysis.

22. The microwave-induced plasma element of claim 1 further including unclad fiber optics for transmitting the laser beam.

23. Method for analyzing the elemental composition of furnace off-gases comprising:

establishing a plasma in an open mesh, refractory waveguide portion exposed to the furnace off-gases;

transmitting emitted plasma light to a spectrometer;

dispersing the emitted light with a spectrometer;

detecting the dispersed light with a detector; and analyzing the detected light with a computer to determine the elemental composition.

24. The method of claim 23 further comprising calibrating the emission levels for quantitative measurements with a calibration source, the calibrating step comprising:

injecting an element to be analyzed from a solid plate of a known matrix of elements by laser ablation;

exciting the injected element in the plasma;

detecting emitted plasma light; and controlling the spectrometer tuning and the calibration source with a computer that processes data received from the detector.

* * * * *

UNITED STATES PATENT AND TRADEMARK OFFICE
CERTIFICATE OF CORRECTION

PATENT NO. : 5,479,254
DATED : December 26, 1995
INVENTOR(S) : Paul P. Woskov, et al It is certified that error appears in the above-indentified patent and that said Letters Patent is hereby corrected as shown below:

Delete Drawing Sheets, 2-3 and substitute therefor the Drawing Sheet, consisting of Fig. 2-3, as shown on the attached pages.

UNITED STATES PATENT AND TRADEMARK OFFICE
CERTIFICATE OF CORRECTION

PATENT NO. : 5,479,254
DATED : December 26, 1995
INVENTOR(S) : Woskov et al

It is certified that error appears in the above-indentified patent and that said Letters Patent is hereby corrected as shown below:

Column 3, line 36: please delete "matrice"; and insert therefor -- material --.

Column 6, line 1: please delete "plasm"; and insert therefor -- plasma --.

Column 6, line 3: please delete "plasm"; and insert therefor -- plasma --.

Column 6, line 6: please delete "plasm"; and insert therefor -- plasma --.

Column 6, line 11: please delete "plasm"; and insert therefor -- plasma --.

Column 6, line 17: please delete "plasm"; and insert therefor -- plasma --.

Column 6, line 17: please delete "i"; and insert therefor --1--.

Column 6, line 19: please delete "plasm"; and insert therefor -- plasma --.

Column 6, line 22: please delete "plasm"; and insert therefor -- plasma --.

Column 6, line 30: please delete "plasm"; and insert therefor -- plasma --.

UNITED STATES PATENT AND TRADEMARK OFFICE
CERTIFICATE OF CORRECTION

PATENT NO. : 5,479,254
DATED : December 26, 1995
INVENTOR(S) : Woskov et al

It is certified that error appears in the above-indentified patent and that said Letters Patent is hereby corrected as shown below:

Column 6, line 45: please delete "plasm"; and insert therefor -- plasma --.

Column 6, line 47: please delete "plasm"; and insert therefor -- plasma --.

Column 6, line 49: please delete "plasm"; and insert therefor -- plasma --.

Column 6, line 52: please delete "plasm"; and insert therefor -- plasma --.

Column 6, line 55: please delete "plasm"; and insert therefor -- plasma --.

Column 6, line 58: please delete "plasm"; and insert therefor -- plasma --.

Column 6, line 63: please delete "plasm"; and insert therefor -- plasma --.

Signed and Sealed this

Twenty-fourth Day of September, 1996

Attest:

BRUCE LEHMAN

*Attesting Officer*         *Commissioner of Patents and Trademarks*